United States Patent [19]
Kreher et al.

[11] Patent Number: 5,158,676
[45] Date of Patent: Oct. 27, 1992

[54] CHROMATOGRAPHY APPARATUS

[75] Inventors: Klaus Kreher, Münster; Gerhard Münch, Gross-Umstadt; Ernst Rogler, Weiterstadt, all of Fed. Rep. of Germany

[73] Assignee: Merck Patent Gesellschaft mit Beschraenkter Haftung, Darmstadt, Fed. Rep. of Germany

[21] Appl. No.: 617,755

[22] Filed: Nov. 26, 1990

[30] Foreign Application Priority Data

May 25, 1990 [DE] Fed. Rep. of Germany ....... 4016760

[51] Int. Cl.$^5$ ............................................. B01D 15/08
[52] U.S. Cl. ................... 210/198.2; 210/349; 210/656; 55/386
[58] Field of Search ................ 210/656, 198.2, 349; 55/67, 386

[56] References Cited

U.S. PATENT DOCUMENTS

| | | | |
|---|---|---|---|
| 3,487,938 | 1/1970 | Patterson | 210/198.2 |
| 3,510,271 | 5/1970 | Emneus | 210/198.2 |
| 3,826,373 | 7/1974 | Andreotti | 210/198.2 |
| 3,932,067 | 1/1976 | Ball et al. | 417/339 |
| 3,934,456 | 1/1976 | Munk | 210/198.2 |
| 3,966,609 | 6/1976 | Godbille | 210/198.2 |
| 3,975,946 | 8/1976 | Ball et al. | 73/61.1 C |
| 4,361,482 | 11/1982 | Teetz | 210/198.2 |
| 4,427,029 | 1/1984 | Charney | 210/198.2 |
| 4,548,713 | 10/1985 | Schmid | 210/198.2 |
| 4,587,993 | 5/1986 | Hartl | 210/198.2 |
| 4,597,866 | 7/1986 | Couillard | 210/198.2 |
| 4,629,562 | 12/1986 | Kercher | 210/198.2 |
| 4,636,315 | 1/1987 | Allen | 210/656 |
| 4,737,292 | 4/1988 | Ritacco | 210/198.2 |
| 4,769,141 | 9/1988 | Couillard | 210/198.2 |
| 4,794,954 | 1/1989 | Tokuda | 210/198.2 |
| 4,865,728 | 9/1989 | Larsson | 210/198.2 |
| 4,891,133 | 1/1990 | Colvin | 210/198.2 |
| 4,927,531 | 5/1990 | Sakamoto | 210/198.2 |

FOREIGN PATENT DOCUMENTS 0271378  6/1988  European Pat. Off. .......... 210/198.2

OTHER PUBLICATIONS

Verzele et al., "Column Hardware in Preparative Liquid Chromatography with Axial Flow," Journal of Chromatography, 450, pp. 47-69 (1988).

*Primary Examiner*—Ernest G. Therkorn
*Attorney, Agent, or Firm*—Millen, White & Zelano

[57] ABSTRACT

Chromatography systems with devices for compressing the column packing and/or for pulsation damping have incorporate an additional device in which a preselected minimum pressure, which is independent of the eluent pressure, is combined with a second pressure component which is proportional to the eluent pressure.

6 Claims, 6 Drawing Sheets

CHROMATOGRAPHY APPARATUS

BACKGROUND OF THE INVENTION

The invention relates to novel, improved chromatography apparatus and methods consisting, as a minimum, of a chromatography column with a device for the axial compression of the column packing and/or of a pulsation-damping device and of an elution device.

In chromatographic separations of substances, especially in liquid chromatography, different pressures for the supply of eluent are necessary, depending on the desired flow rate, the viscosity of the eluent and the resistance to flow of, in particular, the separating column.

The operation of the varying operating pressures on the separating material in the column leads to stress thereon, so that the reproducibility of separation runs and the useful life of the column material may both deteriorate.

One method for solving this problem is disclosed in EP 0 271 378: the eluent provides, with its own pressure via a pressure-transmission arrangement and a device for compressing the separation material, the required backpressure which automatically adjusts to the operating state of the chromatography system. However, this compressive pressure collapses on switching the system off or on malfunctioning of the eluent pump. This results in the separating material in the column continuing to be mechanically stressed in a disadvantageous manner by consecutive compression and relaxation modes.

Another problem is that the operation of eluent pumps is not free of pulsations so that this too results in a mechanical stress on the complete system. The pulsation-damping devices employed for damping the pressure pulses operate only in a very narrow pressure range and thus lose efficacy under varying operating conditions. This is because the pressure of the eluent may vary within wide limits (about 10 to 250 bar).

It has now been found that improved chromatography systems can be provided in which a pressure composed of two components is applied to constructional elements such as a compression or a pulsation damping device. One of these two pressure components is proportional to the eluent pressure and the additional one is a constant minimum pressure.

SUMMARY OF THE INVENTION

Hence, the invention relates to chromatography systems at least consisting of a chromatography column with a device for the axial compression of the column packing and/or of a pulsation-damping device and of an elution device, characterized in that additionally provided is a means which combines a preselected minimum pressure, which is independent of the eluent pressure, with a second pressure component which is proportional to the eluent pressure.

It has been found that the object can be achieved according to the invention by exposing the working medium, for example hydraulic oil or a gas such as air to a pressure-transmission means, and additionally allowing a means for generating a constant pressure, for example a pump or a spring-tensioned movable piston in a cylinder, to act.

The invention additionally relates to chromatographic separation methods characterized in that the chromatography system according to the invention is used.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
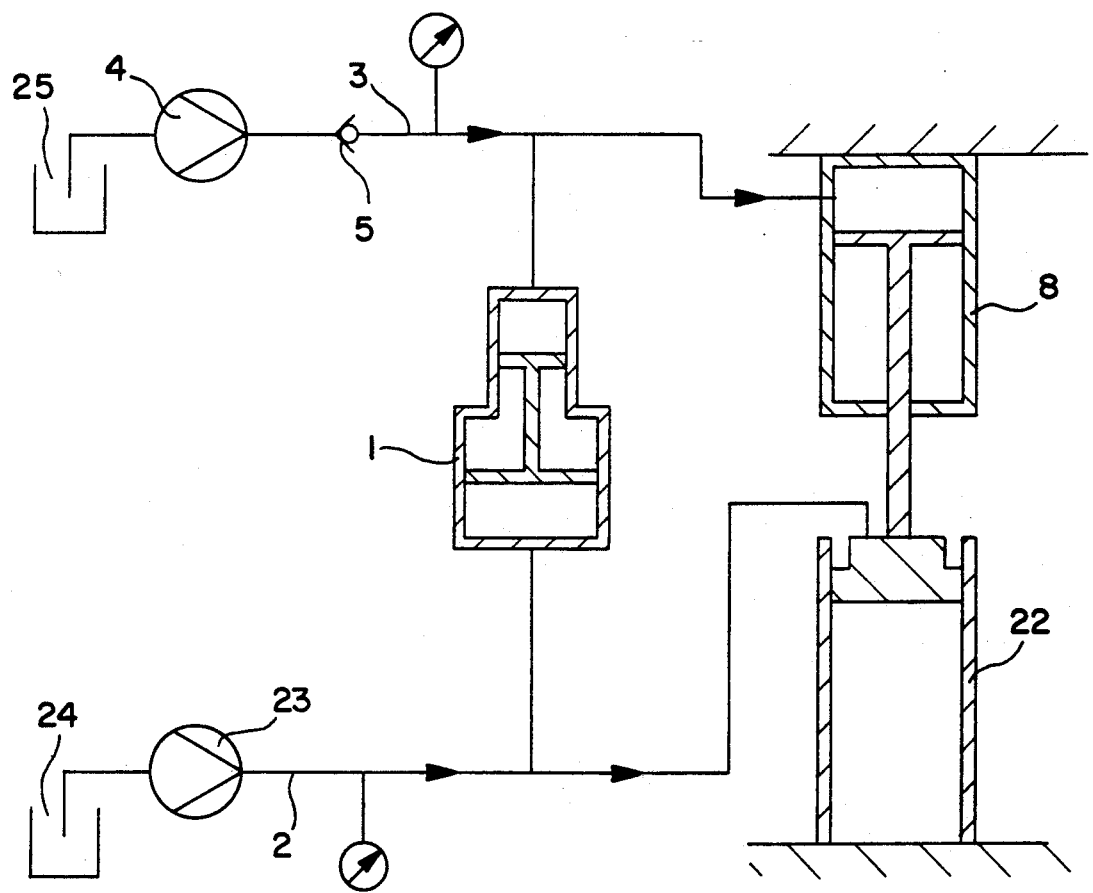
FIG. 1 is a schematic view of a first embodiment of the invention showing a device for axial compression of the column packing comprising a pressure transmission device together with a pump with a check valve and a reservoir for hydraulic fluid as generating means for the constant pressure component.
Figure 2:
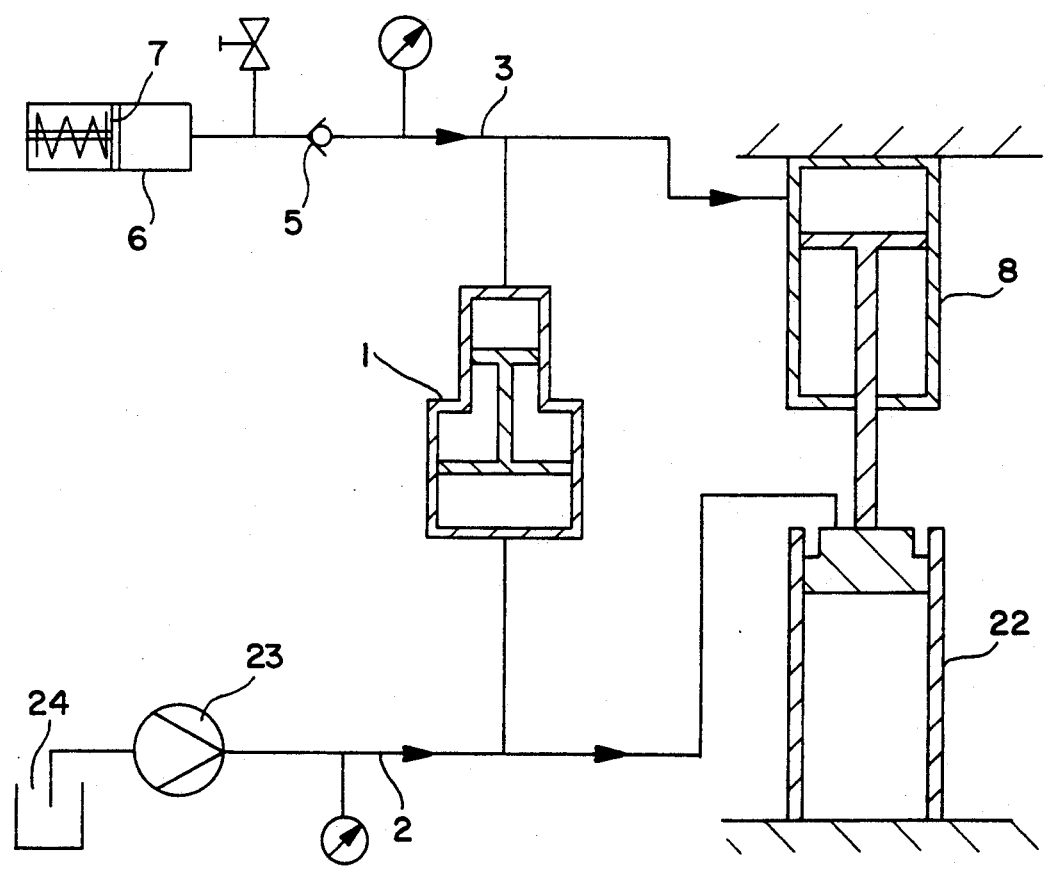
FIG. 2 is a view similar to FIG. 1 but utilizing a hydraulic cylinder as generating means for the constant pressure component.

A chromatography system according to the invention is depicted in FIGS. 1 and 2 and contains essentially the following elements: at least one pressure-transmission device (1) which transfers the pressure of the eluent (2) with a suitable transmission ratio to a hydraulic fluid (3) so that the force acting on the piston of the compression arrangement (8) is a factor in the region of 1.05 to 1.6, preferably 1.2–1.4, greater than the force effective on the eluent side. As long as the pressure on the pressure transmitter on the side of the hydraulic oil is less than the preselected compressive pressure, a device provides a constant pressure. Various devices of this type are known in the prior art and can be employed according to the invention. As an example of such devices, FIG. 1 shows a pump (4) with a check valve (5) and a reservoir for hydraulic fluid (25). FIG. 2 shows as another example a cylinder (6) with movable piston (7) which is subject to an adjustable spring tension. The chromatography column is identified by (22), the elution pump by (23) and the eluent reservoir by (24).

In each case, a device of this type provides a selected minimum compressive pressure. If the eluent pressure increases so that the pressure on the pressure transmitter (1) on the side of the hydraulic oil is greater than the preselected compressive pressure, the check valve (5) closes and the required increase compressive pressure is applied to the column packing.

Figure 3:
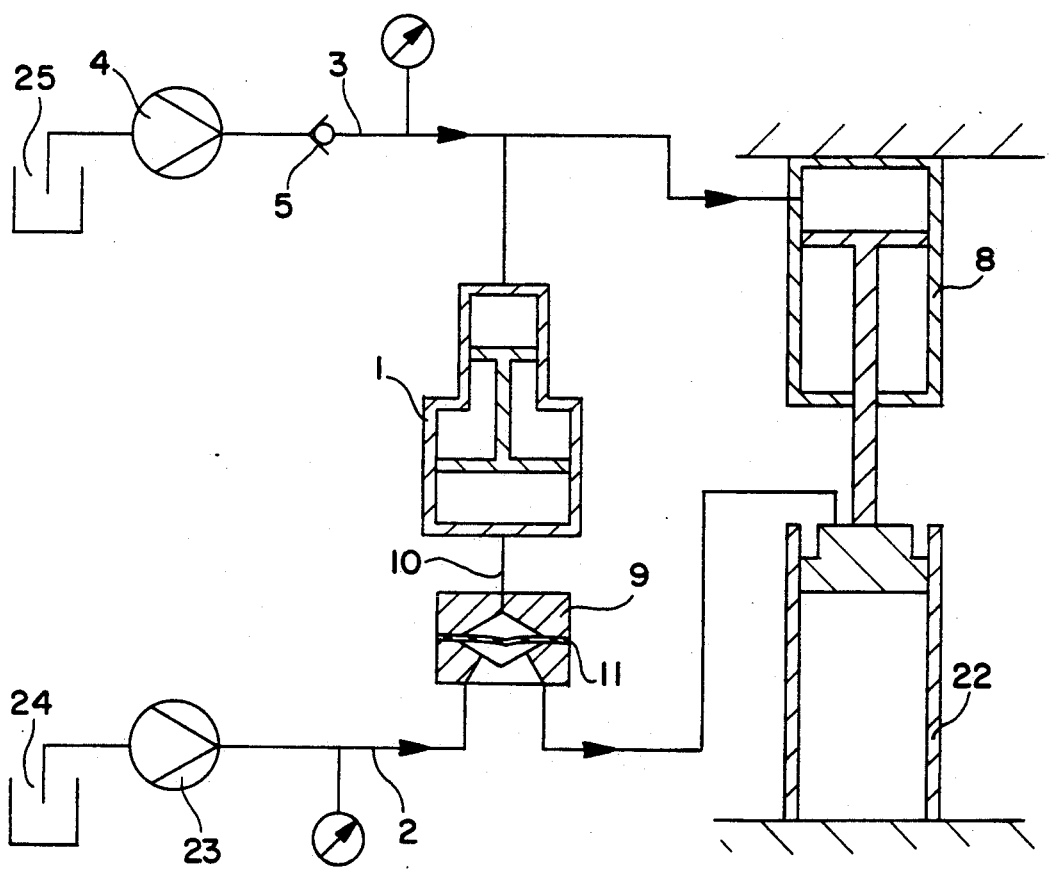
FIG. 3 is a view similar to FIG. 1 of a second, preferred embodiment of the invention employing a pressure transfer device in combination with a pressure transmission device.

A preferred embodiment of the chromatography system according to the invention is depicted in FIG. 3. In this case, a pressure-transfer device (9) is additionally inserted between the eluent (2) and the pressure-transmission device (1). The former transfers the pressure of the eluent (2) to a hydraulic fluid (10) which is separated from the eluent by a solvent-resistant and elastic diaphragm (11).

This preferred embodiment has other important advantages over the state of the art as disclosed, for example, in the publication EP 0 271 378: the dead volume on the eluent side is considerably reduced, in addition the eluent flows through the pressure-transfer arrangement. This is why when the eluent is changed, for example in the frequently used gradient elution, no disturbances of the gradient due to mixing occur. Moreover, diaphragms of this type are more resistent to the eluents used and, in addition, exhibit leaks less often than is the case with sliding seals.

Figure 4:
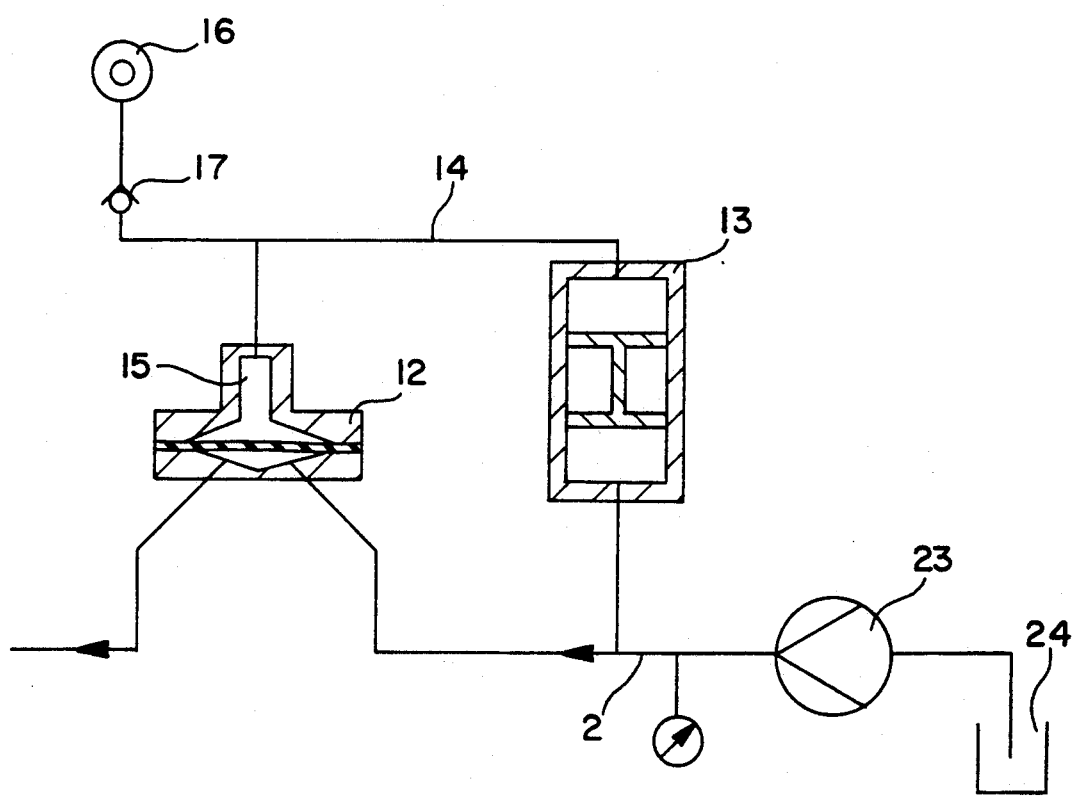
FIG. 4 is a schematic view of a third embodiment of the invention wherein a pulsation-damping device is employed in combination with a pressure transmission device.

In another embodiment of the invention as depicted in FIG. 4, a pulsation-damping device (12) is equipped with a pressure-transmission device (13). The latter transfers the pressure of the eluent (2) to a gas, for example air (14), with which a chamber (15) of the pulsation damper is filled. Additionally present is a device for generating a constant pressure, for example compressor (16) with a check valve (17), in order to provide the chamber (15) of the pulsation-damping device with a minimum pressure.

Figure 5:
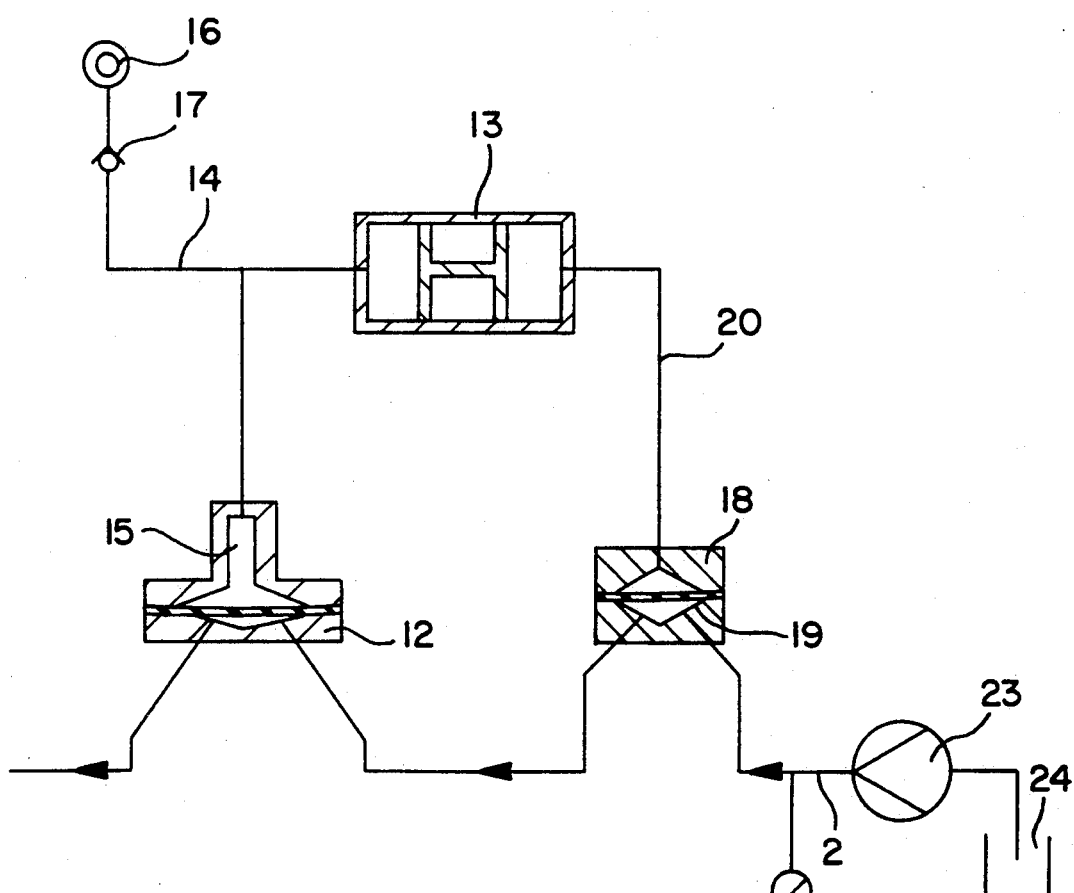
FIG. 5 is a schematic view of a fourth embodiment of the invention similar to FIG. 4 wherein a pulsation damping device is employed with a combination of a pressure transfer device and a pressure transmission device.

A preferred embodiment of the arrangement described last (see FIG. 5) contains an additional pressure-transfer device (18) which transfers the pressure of the eluent (2), using a solvent-resistant and elastic diaphragm (19), to a hydraulic fluid (20). The latter transfers the pressure via the pressure-transmission device (13) to the air (14) with which the chamber (15) of the pulsation-damping device (12) is filled.

Figure 6:
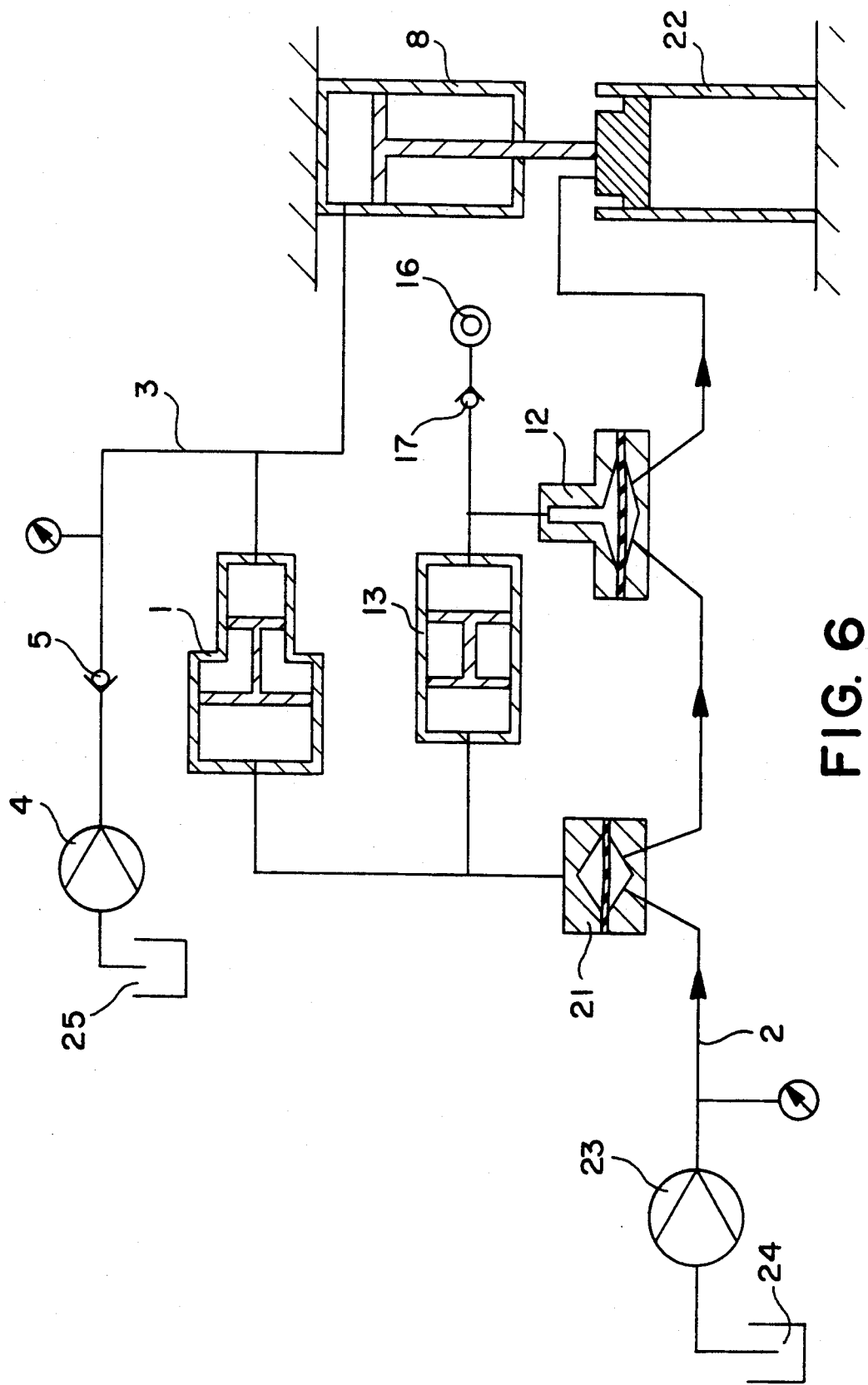
FIG. 6 is a fifth embodiment of the invention utilizing a common pressure-transfer device for both a compression and pulsation device.

In another possible embodiment (see FIG. 6), a common pressure-transfer device (21) serves for both arrangements: both for the compression device and for the pulsation damping device.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, cited above and below, and of corresponding application Federal Republic of Germany P 40 16 760.7, filed May 25, 1990, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Apparatus for axially compressing packing is a chromatography column into which an eluent is introduced under pressure, the apparatus comprising:
   a piston disposed within the column adjacent one end of the column;
   means in communication with the column for introducing the eluent into the column;
   means for applying pressure to the eluent;
   an eluent line connecting the pressure applying means and eluent introducing means to one another
   force applying means connected to the piston for urging the piston to axially pressurize the packing and eluent in the column;
   hydraulic pressurizing means connected by a hydraulic line to the force applying means, and
   pressure transmitting means connecting the hydraulic line to the eluent line.

2. The apparatus of claim 1 wherein the pressure transmitting means comprises a cylinder having first and second faces, the first face having an area larger than the second face, thereon defining first and second chambers within the cylinder with the first chamber connected to the eluent line and the second chamber connected to the hydraulic line.

3. The apparatus of claim 2 wherein the hydraulic line includes a check valve therein which closes when the pressure in the eluent line exceeds a predetermined pressure.

4. The apparatus of claim 3 further including pressure transferring means disposed between the eluent line and the first chamber of the pressure transmitting means.

5. The apparatus of claim 1 wherein the hydraulic line includes a check valve therein which closes when the pressure in the eluent line exceeds a predetermined pressure.

6. The apparatus of claim 5 further including pressure transferring means disposed between the eluent line and hydraulic line.

* * * * *